United States Patent [19]
Cook et al.

[11] 3,966,717
[45] June 29, 1976

[54] 7-β-ACYLAMIDO-3-CARBAMOYLOXYMETHYLCEPH-3-EM-4-CARBOXYLIC ACIDS AND SALTS THEREOF

[75] Inventors: Martin Christopher Cook; Gordon Ian Gregory, both of Chalfont St. Peter; Janice Bradshaw, Harrow, all of England

[73] Assignee: Glaxo Laboratories Limited, Greenford, England

[22] Filed: Nov. 8, 1973

[21] Appl. No.: 413,970

Related U.S. Application Data

[63] Continuation-in-part of Ser. No. 304,524, Nov. 7, 1972, abandoned, which is a continuation-in-part of Ser. No. 252,666, May 12, 1972, abandoned.

[30] Foreign Application Priority Data

May 14, 1971 United Kingdom............... 15082/71
Oct. 1, 1971 United Kingdom............... 45884/71
Aug. 21, 1973 United Kingdom............... 39645/73

[52] U.S. Cl............................ 260/243 C; 424/246
[51] Int. Cl.$^2$........................................ C07D 501/20
[58] Field of Search................................ 260/243 C

[56] References Cited
UNITED STATES PATENTS 3,546,219 12/1970 Long et al....................... 260/243 C
3,573,294 3/1971 Long et al....................... 260/243 C

*Primary Examiner*—Nicholas S. Rizzo
*Attorney, Agent, or Firm*—Bacon & Thomas

[57] ABSTRACT

The invention provides novel antibiotic compounds comprising 7β-acylamido-3-carbamoyloxymethylceph-3-em-4-carboxylic acids and non-toxic derivatives thereof wherein the acylamido group has the structure

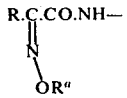

in which R is a carbocyclic or heterocyclic aryl group and $R^a$ is a lower alkyl, cycloalkyl or phenyl group. The compounds are syn isomers or exist as mixtures containing at least 75% of the syn isomer. These antibiotic compounds possess high antibacterial activity against a range of gram positive and gram negative organisms coupled with particularly high stability to β-lactamases produced by various organisms and stability in the presence of human serum. The invention is also concerned with the administration of the compounds.

1 Claim, No Drawings

7-β-ACYLAMIDO-3-CARBAMOYLOXYMETHYL-CEPH-3-EM-4-CARBOXYLIC ACIDS AND SALTS THEREOF

CROSS REFERENCE TO RELATED APPLICATIONS.

This application is a continuation-in-part of U.S. Application Ser. No. 304,524 filed Nov. 7, 1972, which is in turn a continuation-in-part of U.S. Application Ser. No. 252,666 filed May 12, 1972 and now abandoned.

This invention is concerned with improvements in or relating to antibiotics of the cephalosporin series.

The cephalosporin compounds referred to in this specification are generally named with reference to cepham (*J.Amer. Chem.Soc.* 1962, 84, 3400). The term "cephem" refers to the basic cepham structure with one double bond.

As is well known, antibiotics of the cephalosporin series are 7β-acylamido-ceph-3-em-4-carboxylic acids and their various non-toxic derivatives e.g. salts, esters, lactones (if such can be formed), amides, hydrates or the corresponding sulphoxides. These antibiotics may contain various substituents, particularly at the 3-position, including unsubstituted methyl and methyl groups substituted with a variety of substituents as is described in the literature.

The cephalosporin antibiotics of the present invention are characterized in that the compound carries a carbamoyloxymethyl group at the 3-position and that the 7β-acylamido group is a 2-aryl-2-(etherified oxyimino) acetamido group, the compounds being syn isomers or mixtures wherein the syn isomeric form predominates.

The compounds of the invention are defined as having the syn (cis) isomeric form as regards the configuration of the group $OR^a$ with respect to the carboxamido group. The syn configuration is structurally denoted thus:-

$$R.\underset{\underset{OR^a}{\overset{\|}{N}}}{C}.CO.NH-$$

The configuration is assigned on the basis of the work of Ahmad and Spencer (Can J. Chem., 1961, 39, 1340).

The compounds of the present invention may be represented by the general formula (where R represent a monocyclic aryl group which is either a carbocyclic group or a 5- or 6- membered heterocyclic group containing at least one heteroatom selected from O. N and S and $R^a$ represents a $C_1$–$C_4$ alkyl group, a $C_3$–$C_7$ cycloalkyl group or a phenyl group) and non-toxic derivatives of these acids.

The compounds exist as the syn isomers. However mixtures of such syn isomers and the corresponding anti isomers wherein the syn configuration predominates (i.e. mixtures containing at least 75%, preferably at least 90%, of the syn isomer) are also embraced by the invention.

The term "non-toxic" as applied to derivatives of the compounds of the invention means those derivatives which are physiologically acceptable in the dosage at which they are administered. Such derivatives may include, for example, salts, biologically acceptable esters and hydrates.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine, dibenzylethylenediamine, ethanolamine, diethanolamine, triethanolamine and N-methylglucosamine, salts and (b) acid addition salts, e.g. with hydrochloric, hydrobromic, sulphuric, nitric, phosphoric, toluene-p-sulphonic and methane sulphonic acids. The salts may also be in the form of resinates, formed e.g. with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinyl-benzene containing the appropriate groups.

Biologically acceptable esters which may be formed from the compounds according to the invention include those formed with alcohols of the formula $R^4.CO.O.CHR^3.OH$ wherein $R^3$ is hydrogen or lower alkyl and $R^4$ is hydrogen, lower alkyl, lower alkoxy, $C_5$-$C_7$ cycloalkyl, aryl e.g. phenyl, aralkyl e.g. benzyl, lower cycloalkylalkyl, 5- or 6-membered heterocyclic containing O, N or S, lower alkyl substituted by such a heterocyclic group, or the group $-(CH_2)_n.CR^7R^8.NR^5R^6$ where $n$ is 0 or an integer of from 1–5. $R^5$, $R^6$ and $R^7$ are hydrogen or a lower alkyl group and $R^8$ is hydrogen or a lower alkyl, lower alkoxy, lower carbalkoxy or aryl group, a 5- or 6-membered heterocyclic group containing O, N or S or a carbocyclic or heterocyclic aryl lower alkyl group, or any two of the groups $R^5$, $R^6$, $R^7$ and $R^8$ may together form a 5- or 6-membered ring with the adjacent N- or C-atom.

Such esters may also be formed with alcohols of the formula $CHR^9R^{10}OH$ where $R^9$ is lower alkanoyl, substituted or unsubstituted aroyl (carbocyclic or heterocyclic), cyano, lower alkylthio, lower alkoxy, aryloxy e.g. phenoxy, lower carbalkoxy, carbobenzoxy, carbophenoxy, substituted or unsubstituted carbamoyl, lower alkyl sulphonyl or substituted imino such as N-phthalimido, and $R^{10}$ is hydrogen or, where $R^9$ is lower alkanoyl, may be lower alkyl or, where $R^9$ is lower carbalkoxy, may also be lower carbalkoxy.

The aryl group R in the above formula I may, for example, be a phenyl group or a phenyl group substituted by one or more of halo (e.g. chloro or bromo as in p- chlorophenyl), hydroxy (as in p-hydroxyphenyl), lower alkyl (e.g. methyl), nitro, amino, lower alkylamino (e.g. methylamino), di (lower alkyl) amino (e.g. dimethylamino), lower alkanoyl (e.g. acetyl), lower alkanoylamido (e.g. acetamido), lower alkoxy (e.g. methoxy or ethoxy) and lower alkylthio (e.g. methylthio) (the qualification "lower" indicates that the groups so designated may contain 1-6, e.g. 1-4 carbon atoms). Where R is a heterocyclic aryl group this may be, for example, thien-2-yl, thien-3-yl, furyl such as fur-2-yl, pyridyl such as pyrid-3-yl or pyrid-4-yl, pyrrolyl, N-substituted pyrrolyl e.g. N-methylpyrrolyl, isothiazolyl, thiadiazolyl, oxadiazolyl, 3- or 4-isoxazolyl or substituted 3- or 4-isoxazolyl, e.g. a 3-aryl-5-methylisoxazol-4-yl group wherein the aryl group is, for example, phenyl or halophenyl. Heterocyclic groups such as thienyl, furyl or pyridyl may if desired be substituted by any of the substituents described above for phenyl groups.

As indicated above, the group $R^a$ in formula I represents an alkyl group containing 1-4 carbon atoms i.e. a methyl, ethyl, n-propyl, isopropyl, n-butyl, sec-butyl or t-butyl group; a cycloalkyl group containing 3-7 carbon atoms, e.g. a cyclopropyl, cyclopentyl, cyclohexyl or cycloheptyl group; or a phenyl group.

The compounds of the invention, including the non-toxic derivatives thereof, are characterized by their high antibacterial activity against a range of gram-positive and gram-negative organisms, their particularly high stability to β-lactamases produced by various gram negative organisms, and their stability in the presence of human serum.

The properties possessed by the compounds according to the invention render them useful in the treatment of a variety of diseases caused by pathogenic bacteria in human beings and animals.

An important compound falling within general formula I by virtue of its broad spectrum antibiotic properties; stability in the presence of human serum; high stability to β-lactamases produced by a variety of organisms; and resistance to the action of mammalian esterases is 3-carbamoyloxymethyl-7β-[2-methoxyimino-2-(fur-2-yl)-acetamido]-ceph-3-em-4-carboxylic acid (syn isomer), having the formula

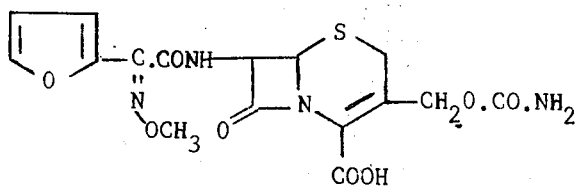

for example as its sodium or potassium salt.

According to one embodiment of the invention we provide a process for the preparation of a compound of general formula I as hereinbefore defined and derivatives thereof which comprises either (a) condensing a compound of the formula

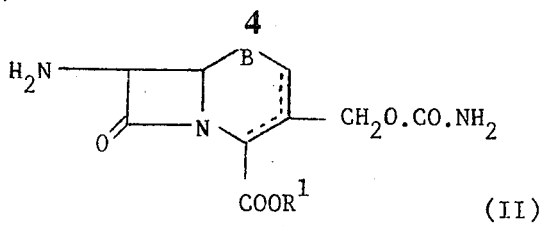

(wherein B is >S or >S → O, $R^1$ is hydrogen or a caboxyl blocking group and the dotted line bridging the 2-, 3- and 4-positions of formula (II) indicates that the compound may be a ceph-2-em or a ceph-3-em compound) with an acylating agent corresponding to the acid.

(wherein R and $R^a$ have the above-defined meanings) or with an acylating agent corresponding to an acid which is a precursor for the acid (III); or (B) reacting a compound of the formula

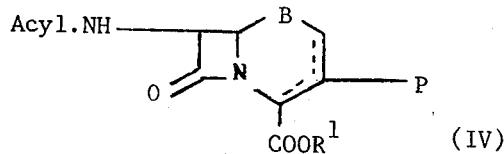

(wherein Acyl is the group

or a precursor therefor;
B, $R^1$ and the dotted line have the above meanings and P is a precursor for the desired carbamoyloxymethyl substituent at the 3-position with a reagent or reagents serving to produce said carbamoyloxymethyl group; whereafter, if necessary and desired in each instance, any of the following reactions (C) are carried out (i) conversion of a precursor for the desired

group into that said group, (ii) conversion of a Δ² isomer into the desired Δ³ isomer, (iii) removal of any carboxyl blocking groups, and (iv) reduction of a compound in which B is >S → O to form the desired B=>S compound; and (D) recovering the desired compound of formula (I), after separation of isomers if necessary.

Salts of the compound according to the invention may be formed in any convenient way. For example base salts may be formed by reaction of the cephalosporin acid with sodium or potassium 2-ethylhexanoate.

In practice it is convenient to condense an acylating agent corresponding to the acid of formula (III) with an amino compound of formula (II) where B and the dotted line have the above defined meanings and $R^1$ is hydrogen or a carboxyl blocking group [e.g. the residue of an ester-forming alcohol (aliphatic or araliphatic), phenol, silanol or stannanol or a symmetrical or mixed If desired, one can first prepare a compound of formula

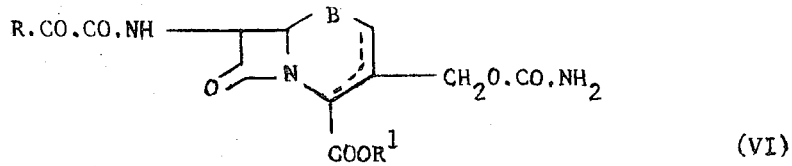

(VI)

anhydride group derived from an appropriate acid] or a derivative thereof, e.g. a salt such as a tosylate or an N-silyl derivative, the condensation optionally being effected in the presence of a condensation agent, and being followed, if necessary, by removal of a carboxyl blocking group $R^1$.

Compounds of formula I may thus be prepared by employing as the acylating agent an acid halide, particularly an acid chloride or bromide, corresponding to the acid (III). Such acylations may be effected at temperatures of from −50° to +50°C, preferably −20° to +30°C. The acylation may be effected in aqueous or non-aqueous media.

Acylation with an acid halide may be effected in the presence of an acid binding agent, e.g. a tertiary amine such as triethylamine or dimethylaniline, an inorganic base such as calcium carbonate or sodium bicarbonate, or an oxirane, which serves to bind hydrogen halide liberated in the acylation reaction. Where an oxirane is employed for this purpose this is preferably a lower-1,2-alkylene oxide such as ethylene oxide or propylene oxide.

Alternatively the free acid form of a compound of formula (III) may itself be used as the acylating agent. Such acylations are desirably conducted in the presence of, for example, a carbodiimide such as N,N'-diethyl-, dipropyl- or diisopropylcarbodiimide, N,N'-dicyclohexylcarbodiimide, or N-ethyl-N'-γ-dimethylaminopropylcabodiimide; a carbonyl compound such as carbonyldiimidazole; or an isoxazolinium salt such as N-ethyl-5-phenylisoxazolinium-3'-sulphonate or N-t-butyl-5-methylisoxazolinium perchlorate. The condensation reaction is desirably effected in an anhydrous reaction medium, e.g. methylene chloride, dimethylformamide or acetonitrile.

Alternatively, acylation may be effected with other amide-forming derivatives of the free acid (III) such as, for example, a symmetrical anhydride or mixed anhydride, e.g. with pivalic acid or formed with a haloformate such as a lower alkylhaloformate. The mixed or symmetrical anhydrides may be generated in situ. For example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid). Another convenient acylating agent is an activated ester e.g. a compound of the formula

(V)

where R and $R^a$ are as defined above and W is, for example, an azide, oxysuccinimide, oxybenztriazole, pentachlorophenoxy or p-nitrophenoxy group.

(where B, R, $R^1$ and the dotted line have the above defined meanings) and then effect reaction of the compound of formula (VI) with an etherified hydroxylamine of formula $R^a$ O.NH$_2$ ($R^a$ having the above defined meaning), followed, if necessary, by removal of the group $R^1$. The reaction product may be separated to give the required syn isomer before or after removal of $R^1$.

If desired, the transformation of a precursor group at the 3-position may be carried out after acylation of an appropriate 7-amino cephalosporin to yield a compound of formula (IV) has taken place.

In general the desired 3-carbamoyloxymethyl group and precursors therefor may be introduced by conventional methods. Thus, for example, a 3-hydroxymethyl cephalosporin may be reacted with an isocyanate of formula $R^2$.NCO (wherein $R^2$ represents a labile substituent group) to give a compound containing a precursor group P of formula —CH$_2$O.CO.NHR$^2$ (where $R^2$ has the above defined meaning) at the 3-position; such precursor groups may be converted to the desired 3-carbamoyloxymethyl group by subsequent cleavage of the group $R^2$, e.g. by hydrolysis. Labile groups $R^2$ which are readily cleavable upon such subsequent treatment include chlorosulphonyl and bromosulphonyl (see German OLS 2,203,653); aralkyl groups such as benzyl, p-methyloxybenzyl and diphenylmethyl; lower alkyl groups such as t-butyl; and halogenated lower alkanoyl groups such as trichloroacetyl.

It may be convenient to retain or even to introduce an N-substituting group $R^2$ during certain transformations of intermediate 3-carbamoyloxymethyl compounds in order to minimise unwanted side reactions involving the carbamoyl group.

3-Hydroxymethyl starting materials for use in the process of this embodiment of the invention may be prepared by, for example, the methods described in British Pat. No. 1,121,508 or our copending Application Ser. No. 304,524.

As indicated above, starting materials of formula II may if desired be employed in the form of acid addition salts, e.g. with hydrochloric, hydrobromic, sulphuric, nitric, phosphoric, toluene-p-sulphonic or methane sulphonic acids.

Any blocking group substituting the 4-carboxyl group of a compound of formula II, IV or VI is preferably formed with an alcohol (aliphatic or araliphatic), phenol, silanol, stannanol or acid which contains 1–20 carbon atoms and which may readily be split off at a later stage of the reaction.

Where the compound (II), (IV) or (VI) is an ester, suitable esters include compounds containing at the 4-position an ester group selected from the following list, which is not, however, intended to be an exhaustive list of possible ester groups.

i. COOCR$^b$R$^c$R$^d$ wherein at least one of R$^b$, R$^c$ and R$^d$ is an electron-donor e.g. p-methoxyphenyl, 2,4,6- trimethylphenyl, 9-anthryl, methoxy, acetoxy, or fur-2-yl. The remaining $R^b$, $R^c$ and $R^d$ groups may be hydrogen or organic substituting groups. Suitable ester groups of this type include p-methoxybenzyloxycarbonyl and 2,4,6-trimethylbenzyloxycarbonyl.

ii. $COOCR^bR^cR^d$ wherein at least one of $R^b$, $R^c$ and $R^d$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulponiumethyl, o-nitrophenyl or cyano. The remaining $R^b$, $R^c$, and $R^d$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. $COOCR^bR^cR^d$ wherein at least two of $R^b$, $R^c$ and $R^d$ are hydrocarbon such as alkyl e.g. methyl or ethyl, or aryl e.g. phenyl and the remaining $R^b$, $R^c$ and $R^d$ group, if there is one, is hydrogen. Suitable esters of this type include t-butyloxycarbonyl, t-amyloxycarbonyl, diphenylmethoxycarbonyl and triphenylmethoxycarbonyl.

iv. $COOR^e$ wherein $R^e$ is adamatyl, 2-benzyloxyphenyl, 4-methylthiophenyl, tetrahydrofur-2-yl or tetrahydropyran-2-yl.

v. Silyloxycarbonyl groups obtained by reaction of a carboxyl group with a derivative of a silanol. The derivative of a silanol is conveniently a halosilane or a silazane of the formula

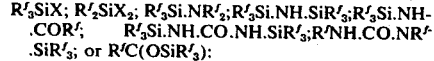 

NSiR′$_3$ where X is a halogen and the various groups R′, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and base-catalysed hydrolysis is generally applicable, as well as enzymically-catalysed hydrolyses; however, aqueous mixtures may be poor solvents for these compounds and they may cause isomerizations, rearrangements, side-reactions, and general destruction, so that special methods may be desirable.

Five suitable methods of deesterification are

1. Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole.

2. Reduction.

Suitable systems for effecting reduction are zinc/acetic acid, zinc/formic acid, zinc/lower alcohol, zinc/pyridine, palladised-charcoal and hydrogen, and sodium and liquid ammonia.

3. Attack by nucleophiles.

Suitable nucleophiles are those containing a nucleophilic oxygen of sulphur atom for example alcohols, mercaptans and water.

4. Oxidative methods, for example, those which involve the use of hydrogen peroxide and acetic acid.

5. Irradiation.

Where at the end of a given preparative sequence compounds are obtained wherein B is $> S \rightarrow O$ and a compound is desired in which B is $> S$ conversion to a sulphide may for example be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°C$.

Alternatively, reduction of the 1-sulphinyl group may be effected by phosphorus trichloride or tribromide in solvents such as methylene chloride, dimethylformamide or tetrahydrofuran, preferably at a temperature of $-20°C$ to $+50°C$.

Where the resultant compound is a ceph-2-em-4-ester the desired ceph-3-em compound may be obtained by treatment of the former with a base.

The acid (III) to which the acylating agent corresponds may be obtained by reacting a glyoxylic acid of formula

R.CO.COOH (where R has the above defined meaning) or an ester thereof with $R^aO.NH_2$ ($R^a$ having the above defined meaning).

The resulting acid or ester may then be separated into its syn and anti isomers e.g. by crystallisation, chromatography or distillation, followed when necessary by hydrolysis of the ester.

Separation of the syn and anti components of an ester derivative of an α-(etherified oxyimino)carboxyclic acid existing as a mixture of the syn and anti isomers may be effected by selective hydrolysis of the ester under basic conditions, since the less sterically hindered anti isomer tends to saponify more rapidly and may thus be removed as the free acid, leaving purified syn ester. The separated syn ester may then be converted to a corresponding acylating agent as desired. This process as described in greater detail in copending Application Ser. No. 304491 of Janice Bradshaw and Godfrey Basil Webb filed Nov. 7th 1972.

The acid (III) may also be prepared by carrying out an O-alkylation or O-arylation type of reaction on a compound of the formula

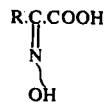

i.e. an 2-hydroxyimino acid, or more preferably on an ester of such an 2-hydroxyimino acid. The desired reaction may be achieved with an organic halide, sulphate or sulphonate, e.g. a compound of formula $R^aJ$ where R$^a$ has the above-defined meaning and J is halogen, sulphate or a sulphonate such as tosylate. Alternatively the 2-hydroxyimino acid or an ester thereof may be reacted with a diazoalkane, e.g. diazomethane, an alkyl fluorosulphonate, e.g. methyl fluorosulphonate, or an alkyloxonium tetrafluoroborate, e.g. a trialkyloxonium tetrafluoroborate such as trimethyloxonium tetrafluoroborate to give the required alkoxyimino acid (III) or an ester thereof, or with diphenyliodonium bromide to give the required phenoxyimino acid (III). Such reactions with a diazo compound, fluorosulphonate or tetrafluoroborate may require assistance, e.g. with a Lewis acid such as BF$_3$.

When converting the acid (III) to a corresponding acylating agent it will be appreciated that any amino groups present in R should desirably be protected to avoid undesirable side reactions; similar protection of amino groups is also desirable when reacting the consequent acylating agent with a compound of formula (II).

Syn and anti isomers may be distinguished by appropriate techniques, e.g. by their ultraviolet spectra, by thin layer or paper chromatography or by their nuclear magnetic resonance spectra. For example, for DMSO-d$_6$ solution compounds of Formula 1 exhibit the doublet for the amide NH at a lower field for the syn isomers than for the anti-isomers. These factors may be employed in monitoring reactions.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt or biologically acceptable ester thereof adapted for use in human or veterinary medicine. Such compositions may be presented for use in conventional manner with the aid of any necessary pharmaceutical carriers or excipients.

The antibacterial compounds according to the invention may be formulated for injection and may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The compositions may be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinyl-pyrrolidone; fillers, for example lactose, sugar, maize-starch, calcium phosphate, sorbitol or glycine; lubricants, for example magnesium stearate, talc, polyethylene glycol or silica; disintegrants, for example potato starch or acceptable wetting agents such as sodium lauryl sulphate. The tablets may be coated according to methods well known in the art. Oral liquid preparations may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles which may include edible oils, for example almond oil, fractionated coconut oil, oily esters, propylene glycol or ethyl alcohol; preservatives, for example methyl or propyl p-hydroxybenzoates or sorbic acid. Suppositories will contain conventional suppository bases, e.g. cocoa butter or other glyceride.

The compositions may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-liquid form, or may be used as drops etc. Topical applications may be formulated in hydrophobic or hydrophilic bases as ointments, creams, lotions, paints, powders etc.

For veterinary medicine the compositions may, for example, be formulated as intramammary preparations in either long acting or quick-release bases.

In general the compositions may contain from 0.1% upwards, preferably from 10–60% of the active material, depending on the method of administration. Where the compositions comprise dosage units, each unit will preferably contain 50–500 mg of the active ingredient. The dosage as employed for adult human treatment will preferably range from 100–3000 mg for instance 1500 mg per day, depending on the route and frequency of administration.

The compounds according to the invention may be administered in combination with other therapeutic agents such as antibiotics, for example penicillins, other cephalosporins or tetracyclines.

The following examples illustrate the invention. All temperatures are in °C, melting points were determined on a Kofler block, and the structures of the products were confirmed by i.r. and n.m.r. spectroscopy and microanalysis.

A. PREPARATION OF STARTING MATERIALS a. Diphenylmethyl 7β-(Thien-2-yl)acetamido-3-trichloroacetyl-carbamoyloxymethylceph-3-em-4-carboxylate.

Trichloroacetyl isocyanate (13.2g, 70mmole) was added to a stirred suspension of diphenylmethyl 3-hydroxymethyl-7β-(thien-2-yl)acetamidoceph-3-em-4-carboxylate (26.0g, 50mmole) in anhydrous acetone (600ml) at 20°. The solid soon dissolved and after the mixture had been stirred at 20° for 1 hour, it was chilled for 1 hour and the resulting solid was filtered off and washed with ether to give the trichloroacetyl carbamate (33.1g, 93%), m.p. 183° to 184°; $[\alpha]_D^{21}$ + 24° (c 0.95 DMSO); $\lambda_{inf.}^{EtOH}$ 235 nm ($\epsilon$ 14,500) and $\lambda_{inf.}^{EtOH}$ 256nm ($\epsilon$8,820).

b. Diphenylmethyl 7β-Amino-3-trichloroacetylcarbamoyloxymethylceph-3-em-4-carboxylate Toluene-p-sulphonic Acid Salt.

Anhydrous pyridine (31ml., 0.384mole) was added to a solution of phosphorus pentachloride (20g., 96mmole) in dry dichloromethane (300ml) at 3°. The suspension was stirred for 10 minutes at 3° and diphenylmethyl 7β-(thien-2-yl) acetamido-3-trichloroacetyl-carbamoyloxymethylceph-3-em-4-carboxylate (22.5g, 32mmole) was added; the reaction was stirred at ca. 2° for 1 hour. The dark solution was poured slowly into a cold (0°) anhydrous mixture of methanol (80ml) and dichloromethane (200ml), with the temperature kept below 5°. The temperature of the solution was then allowed to rise to 23° and, after stirring the solution at this temperature for 1 hour, water (200ml) was added. The organic layer was separated and washed with 2N-sulphuric acid, water, sodium bicarbonate solution and water, dried over magnesium sulphate, and evaporated in vacuo. The resulting oil was dissolved in ethyl acetate and a solution of toluene-p-sulphonic acid monohydrate (6.0g, 31.5mmole) in ethyl acetate was added. The combined solutions (ca. 350ml) were poured into diethyl ether (ca. 1 l.) and the resulting solid was filtered off and dried in vacuo to give the toluene-p-sulphonate salt (17.2g, 72%), m.p. 150° to 153°; $[\alpha]_D^{21°}$ +7.5° (c 0.82 in DMSO); $\lambda_{max}^{EtOH}$ 263nm ($\epsilon$7,600) and $\lambda_{inf.}^{EtOH}$ 267nm ($\epsilon$7,350).

Evaporation of the filtrate and trituration of the residue with ethanol afforded unchanged starting material (3.2g, 14.2%).

c. Diphenylmethyl 7β-Amino-3-carbamoyloxymethylceph-3-em-4-carboxylate Toluene-p-Sulphonic Acid Salt.

The toluene-p-sulphonic acid salt of diphenylmethyl 7β-amino-3-trichloroacetylcarbamoyloxymethylceph-3-em-4-carboxylate (17.2g, 22.7mmole) was dissolved in a mixture of anhydrous methanol (900ml) and acetyl chloride (45ml) and left to stand at 20°for 5 hours. Removal of the solvent under reduced pressure gave an oil, which was dissolved in dichloromethane. This solution was shaken with aqueous sodium bicarbonate solution and then washed with water. Toluene-p-sulphonic acid monohydrate (4.3g, 22.7mmole) was added and the solvent was evaporated in vacuo. The residue was dissolved in hot isopropanol (ca. 150ml) and the solution was poured into diisopropyl ether (ca. 600ml). The precipitated solid was filtered off and dried in vacuo to give the carbamate ester (8.9g, 64%), m.p. 110° to 112°; $[\alpha]_D^{21°}$ −14° (c, 1.0 in CHCL$_3$); $\lambda_{max}^{EtOH}$ 259nm ($\epsilon$6,120) and $\epsilon_{inf.}^{EtOH}$ 227nm ($\epsilon$15,800)

B. EXAMPLES

EXAMPLE 1 a. Diphenylmethyl 3-carbamoyloxymethyl-7β-[2-methoxyimino-2-(fur-2-yl)acetamido]-ceph-3-em-4-carboxylate (syn isomer)

Method (i)

Crude diphenylmethyl 7β-amino-3-carbamoyloxymethylceph-3-em-4-carboxylate toluene-p-sulphonic acid salt obtained from the corresponding 3-trichloroacetylcarbamoyloxymethyl compound (25.0g, 0.33 mole) was dissolved in a mixture of ethyl acetate and aqueous sodium bicarbonate solution. The organic layer was separated, washed with water, dried over magnesium sulphate, and evaporated on a rotary evaporator to give diphenylmethyl 7β-amino-3-carbamoyloxymethylceph-3-em-4-carboxylate (11.5g, 0.262mole, 77%) as a foam.

2-Methoxyimino-2-(fur-2-yl) acetic acid, (syn isomer) (5.32g, 0.312mole) in dry dichloromethane (100ml) was added to a solution of this amine in dichloromethane (50ml) cooled to 3°, followed 10 minutes later by a solution of DL-dicyclohexylcarbodiimide (6.5g, 0.312 mole) in dichloromethane (30ml). The reaction mixture was stirred in an ice-bath for 45 minutes during which time a solid (presumably N,N'-dicyclohexyl urea) crystallised out. This was filtered off and discarded, and the filtrate was washed with aqueous sodium bicarbonate solution and water, dried over magnesium sulphate, and evaporated to dryness. The residue was triturated with ethanol to give a crude product (10.6g) which was purified by chromatography on Silica Gel (1kg). Elution with 10% acetone in dichloromethane removed non-polar impurities, and fractions eluted with 20% acetone in dichloromethane gave the methoxyimino-carbamate ester (4.8g, 31%), m.p. 199° to 202°; $[\alpha]_D^{21°}$ +14° (c, 1.0 in DMSO), $\lambda_{max}^{EtOH}$ 277nm ($\beta$18,600) and $\lambda_{inf.}^{EtOH}$ 270nm ($\epsilon$17,900).

Method (ii)

Triethylamine (1.86g, 18.4mmole) was added to a dichloromethane solution (35ml) of 2-methoxyimino-2-(fur-2-yl)acetic acid (syn isomer) (3.1g, 18.4mmole). After cooling this solution in an ice-bath for 5 minutes, oxalyl chloride (1.57ml, 18.4mmole) and a drop of N,N-dimethylformamide were added. After 0.5 hours the solvent was removed under reduced pressure and the solid residue was dried for 1 hour in vacuo. Anhydrous ether (150ml) was added to dissolve the acid chloride that had been formed and the insoluble triethylamine hydrochloride (2.5g) was filtered off. The ether was evaporated on a rotary-evaporator and the oily residue was redissolved in dichloromethane.

Diphenylmethyl 7β-amino-3-carbamoyloxymethylceph-3-em-4-carboxylate toluene-p-sulphonic acid salt (8.9g, 14.7mmole) was dissolved in anhydrous dichloromethane. This solution was shaken with aqueous sodium bicarbonate solution, washed with water, and dried over magnesium sulphate. To this solution of the free amine were added the dichloromethane solution of 2-methoxyimino-2-(fur-2-yl)acetyl chloride (syn isomer) and propylene oxide (5ml). After 10 minutes a crystalline solid (1.1g) was filtered off, which was subsequently identified as diphenylmethyl 7β-amino-3-carbamoyloxymethylceph-3-em-4-carboxylate hydrochloric acid salt. The filtrate was washed with 2N-sulphuric acid, water, aqueous sodium bicarbonate solution and water, and was dried over magnesium sulphate and evaporated to dryness to yield the methoxyimino carbamate ester (2.5g, 30.5%), similar in physical properties to the product of Method (i) above.

b. Sodium 3-Carbamoyloxymethyl-7β-[2-methoxyimino-2-(fur-2-yl)acetamido]-ceph-3-em-4-carboxylate (syn isomer)

Trifluoroacetic acid (20ml) was added slowly to a mixture of anisole (5ml) and diphenylmethyl 3-carbamoyloxymethyl-7β-[2-methoxyimino-2-(fur-2-yl)acetamido]-ceph-3-em-4-carboxylate (syn isomer) (4.7g, 8 mmole) which had been cooled in an ice-bath. The flask was shaken occasionally during the next 10 minutes to ensure complete solution of the solid. It was then removed from the ice-bath and excess trifluoroacetic acid was removed on a rotary-evaporator. Trituration of the residue with ethyl acetate (5ml) gave 3-carbamoyloxymethyl-7β-[2-methoxyimino-2-(fur-2-yl)acetamido]-ceph-3-em-4-carboxylic acid (syn isomer) (3.3g, 94%) as a solid which was filtered off and washed with diethyl ether.

The free acid was dissolved in acetone and a slight excess of sodium ethyl-2-hexanoate in acetone (8.0ml of a molar solution) was added. After the reaction mixture had been stirred at 0° for 2 hours, the sodium salt (2.3g, 73%) was filtered off. This was combined with another batch of sodium salt (0.8g) and purified by washing an aqueous solution (250ml) with ether (2×100ml., 1×50ml). The aqueous solution was freeze-dried to give sodium 3-carbamoyloxymethyl-7β-[2-methoxyimino-2-(fur-2-yl) acetamido]-ceph-3-em-4-carboxylate (syn isomer) (2.66g), $[\alpha]_D^{21}$ +73.5° (c, 1.06 in DMSO); $\lambda_{max}^{pH\ 6}$ 274nm ($\epsilon$ 16,500); $\nu_{max}$ (Nujol) 3450, 3330, 3250, (NH, NH$_2$ and H$_2$O), 1752 (azetidin-2-one), 1710 (OCONH$_2$), 1665 and 1540 (CONH), and 1625 and 1600 cm$^{-1}$ (carboxylate); $\tau$(DMSO-d$_6$) 0.24 (d,J8Hz, CON$\underline{H}$), 2,12 (d, J2Hz, furyl C$_5$-$\underline{H}$), 3.25 and 3.30 (m,furyl C$_3$-$\underline{H}$ and C$_4$-$\underline{H}$), 3.44 (broad s, CON$\underline{H}_2$), 4.34 (dd, J 5 and 8 Hz, C$_7$-$\underline{H}$), 4.92 (d, J4.5Hz, C$_6$-$\underline{H}$), 5.15 (q, J13Hz, C$_3$-C$\underline{H}_2$), 6.07 (s, NOC$\underline{H}_3$) and 6.58 (q, J 18Hz, C$_2$-$\underline{H}_2$)

Found: C,42.0; H,3.8; N,12.1; S,7.2. C$_{16}$H$_{15}$N$_4$NaO$_8$S.0.5H$_2$O(455.37) requires C,42.2; H,3.5; N,12.3 and S,7.0%).

EXAMPLE 2 a. Diphenylmethyl 3-Carbamoyloxymethyl-7β-[2-phenoxyimino-2-(fur-2-yl)acetamido]-ceph-3-em-4-carboxylate (syn isomer)

A solution of DL-dicyclohexycarbodiimide (7.75g, 0.382mole) in dry dichloromethane (50ml) was added over 10 minutes to a solution of diphenylmethyl 7β-amino-3-carbamoyloxymethylceph-3-em-4-carboxylate (13.7g, 0.312 mole) and 2-phenoxyimino-2-fur-2-yl)acetic acid (syn isomer) (8.8g, 0.382 mole) in dry dichloromethane (200ml) at 0°. After 45 minutes, a solid (presumably N,N'-dicyclohexyl urea) was filtered off, and the filtrate was washed with aqueous sodium bicarbonate solution and water, dried over magnesium sulphate, and evaporated on a rotary evaporator. The residue was chromatographed on a Silica gel (1kg) column. Less polar impurities than the required product were eluted with dichloromethane (1 l.), acetone:dichloromethane=2.98 (1 l.), and acetone:dichloromethane = 5:95 (4 l.). Fractions eluted with acetone:dichloromethane = 10:90 and acetone:dichloromethane = 15:85 were evaporated to a gum (11g) which was triturated with diethyl ether to give a solid (8.35g, 41%). This was filtered off and purified further by crystallisation from aqueous ethanol to give the phenoxyimino carbamate ester (7.6g), m.p. 143° to 146°; $[\alpha]_D^{22°}$ + 48° (c,1.0 in DMSO); $\lambda_{max}^{EtOH}$273nm ($\epsilon$18,700), $\lambda_{inf.}^{EtOH}$ 271nm ($\epsilon$17,600) and $\lambda_{max}^{EtOH}$ 245nm ($\epsilon$ 16,5000).

b. Sodium 3-Carbamoyloxymethyl-7β-[2-phenoxyimino-2-(fur-2-yl) acetamido]-ceph-3-em-4-carboxylate (syn isomer)

Trifluoroacetic acid (30ml) was added over 10 minutes to an ice-cooled mixture of anisole (8ml) and diphenylmethyl 3-carbamoyloxymethyl-7β-[2-phenoxyimino-2-(fur-2-yl)acetamido]-ceph-3-em-4-carboxylate (syn isomer) (7.4g, 11.4mmole). After a further 5 minutes at 0°, the dark solution was carefully poured into a mixture of a saturated aqueous solution of sodium bicarbonate and ethyl acetate. The aqueous solution was separated and treated with activated charcoal. The ethyl acetate layer was washed with water and the aqueous wash was combined with the sodium bicarbonate extract and acidified with concentrated hydrochloric acid. This acidic solution was extracted with a mixture of ethyl acetate and diethyl ether which was then washed 5 times with water, dried over magnesium sulphate, and evaporated in vacuo. The residue was washed with diethyl ether and diisopropyl ether to give the cephalosporin acid (4.5g, 82%) as a solid.

This acid was dissolve in ethyl acetate (150ml) and a solution of sodium ethyl-2-hexanoate in ethyl acetate (10ml., containing 10mmole) was added. The solution was cooled in an ice-bath and stirred for 1.5 hours during which time the product (2.84g) crystallised out, leaving unchanged acid (1.1g was recovered by prepipitation with petrol b.p. 60° to 80°) in solution. The solid was filtered off to give the carbamate sodium salt, $[\alpha]_D^{21}$ +89° (c 0.96 in DMSO); $\lambda_{max}^{pH6}$ 298nm ($\epsilon$15,000) and $\lambda_{max}^{pH6}$ 270nm ($\epsilon$16,700); $\nu_{max}$ (Nujol) 3500 (H$_2$O), 3350, 3270 (NH$_2$ and NH), 1765 (azetidin-2-one), 1710 (OCONH$_2$) and 1690 and 1530 cm$^{-1}$ (COHN); $\tau$(DMSO-d$_6$) -0.10 (d, J8Hz, CON$\underline{H}$), 1.98 (d, J 2Hz, furyl C$_5$-$\underline{H}$), 2.35 to 2.9 (m,NOC$_6$H$_5$), 3.02 (d, J2Hz, furyl C$_3$-$\underline{H}$), 3.22 (dd,J2Hz, furyl C$_4$-$\underline{H}$), 3.43 (broad s, CON$\underline{H}_2$), 4.23 (dd, J 8, 5 Hz, C$_7$-$\underline{H}$), 4.85 (d,J 5Hz, C$_6$-$\underline{H}$), 5.14 (ABq, J 13Hz, C$_3$-CH$_2$) and 6.40 (ABq, J 18 Hz, C$_2$-$\underline{H}_2$) (Found: C,48.2; H,3.8; N,10.5; S,5.9. C$_{21}$H$_{17}$N$_4$NaO$_8$ S.H$_2$O(526.46) requires C,48.2; H,3.6; N,10.7; S,6.1%).

We claim:

1. A compound selected from the group consisting of a cephalosporin antibiotic of the formula

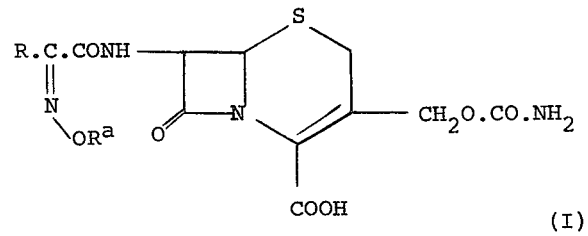

(I)

wherein R is pyrrolyl; N-methylpyrrolyl; isothiazolyl; thiadiazolyl; oxadiazolyl; 3- or 4-isoxazolyl; 3-phenyl-5-methylisoxazol-4-yl or 3-halophenyl-5-methylisoxazol-4-yl; and R$^a$ is C$_{1-4}$ alkyl, C$_{3-7}$ cycloalkyl or phenyl; and a physiologically acceptable salt thereof, said cephalosporin antibiotic being in the form of a syn isomer free of the corresponding anti isomer to the extent of at least 75%.

* * * * *